United States Patent [19]

Elliott et al.

[11] Patent Number: 4,895,589
[45] Date of Patent: Jan. 23, 1990

[54] HETEROCYCLIC COMPOUNDS

[75] Inventors: Raymond Elliott, Nr. Reading; John Dalziel, Binfield, both of England

[73] Assignee: Imperial Chemical Industries PLC, London, England

[21] Appl. No.: 892,364

[22] Filed: Aug. 4, 1986

[30] Foreign Application Priority Data

Aug. 7, 1985 [GB] United Kingdom ................ 8519836

[51] Int. Cl.⁴ ................. A01N 43/653; C07D 249/08
[52] U.S. Cl. ........................................... 71/92; 71/76;
548/101; 548/262
[58] Field of Search ..................... 548/262, 101; 71/92, 71/76

[56] References Cited

U.S. PATENT DOCUMENTS

| | | | |
|---|---|---|---|
| 4,243,405 | 1/1981 | Balasubramanyan et al. | 71/76 |
| 4,507,140 | 3/1985 | Sugavanam | 71/76 |
| 4,622,333 | 11/1986 | Lantzsch et al. | 514/383 |
| 4,634,466 | 1/1987 | Noon et al. | 71/92 |
| 4,655,820 | 4/1987 | Worthington et al. | 71/92 |

OTHER PUBLICATIONS

CA 98:215593e, Sauter et al., (1983), Azole Compounds & Tungicidal Compositions Containing Them.
CA 106:176401c, Ellia et al., (1987).
Burger, Medicinal Chemistry, 2nd Ed., (1960), p. 1055.
Arnoldi et al., *Pesticides Science*, 13:670–678, (1982).

*Primary Examiner*—Richard L. Raymond
*Assistant Examiner*—Patricia L. Morris
*Attorney, Agent, or Firm*—Cushman, Darby & Cushman

[57] ABSTRACT

A triazole derivative having the general formula (I):

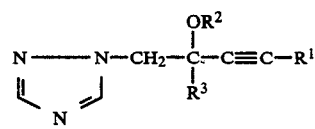

and stereoisomers thereof, wherein $R^1$ is an alkyl group containing from 3 to 6 carbon atoms, or a haloalkyl group containing from 2 to 5 carbon atoms, or a group —$CH_2$—Z where in Z is a cycloalkyl group containing from 3 to 5 carbon atoms, $R^1$ containing primary or secondary carbon atoms only; $R^2$ is hydrogen or an alkyl group containing from 1 to 4 carbon atoms; and $R^3$ is a tertiary butyl group optionally substituted by halogen; and salts, esters and metal complexes of the compound of formula (I) wherein $R^2$ is hydrogen. These compounds are useful as plant growth regulating agents.

8 Claims, No Drawings

HETEROCYCLIC COMPOUNDS

This invention relates to heterocyclic compounds useful as plant growth regulating agents, to processes for preparing them, to compositions containing them and to methods of regulating plant growth using them. In European Patent Publication No. 0052424A there are described certain triazole and imidazole compounds in respect of which details of fungicidal activity are disclosed. The compounds are also stated to be useful for their plant growth regulating effects, although no experimental details are provided. We have now found that certain selected triazole compounds falling within the broad scope of the disclosure of EP No. 0052424 have unexpectedly and surprisingly superior plant growth regulating properties.

According to the present invention there is provided a triazole derivative having the general formula (I)

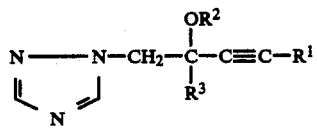

and stereoisomers thereof, wherein $R^1$ is an alkyl group containing from 3 to 6 carbon atoms, or a haloalkyl group containing from 2 to 5 carbon atoms, or a group $-CH_2-Z$ wherein Z is a cycloalkyl group containing from 3 to 5 carbon atoms; $R^2$ is hydrogen or an alkyl group containing from 1 to 4 carbon atoms; and $R^3$ is a tertiary butyl group optionally substituted by halogen; and salts, esters and metal complexes of the compound of formula (I) wherein $R^2$ is hydrogen.

The compounds of the invention may contain chiral centres. Such compounds are generally obtained in the form of racemic mixtures. However, these and other mixtures can be separated into the individual isomers by methods known in the art, and this invention embraces such isomers.

Preferred groups $R^2$ are hydrogen or methyl. Hydrogen is especially preferred.

$R^1$ is preferably an alkyl group containing 4 or 5 carbon atoms. When $R^1$ is a haloalkyl group, it preferably contains a single halogen atom. Preferred halogen atoms are chlorine, bromine and fluorine, and especially chlorine. When $R^1$ is a haloalkyl group it preferably contains 3 or 4 carbon atoms. The group $R^1$ may be a branched or straight chain alkyl group or haloalkyl group and may contain primary, secondary or tertiary carbon atoms. However, the group $R^1$ preferably contains primary or secondary carbon atoms only.

$R^3$ is preferably a tertiary butyl group, optionally substituted by a single halogen atom. Preferred halogen atoms are fluorine, chlorine and bromine, and especially fluorine and chlorine. Z is preferably a cyclopropyl or cyclobutyl group.

The present invention includes salts, esters and metal complexes of the compounds of formula (I) wherein $R^2$ is hydrogen. As examples of esters there may be mentioned for example acetates or benzoates. As examples of salts there may be mentioned for example toluene sulphonate salts, dodecyl benzene sulphonate salts, hydrochloride salts, hydrobromide salts and ortho phosphate salts. Without limitation of the generality of the above statement, the present invention also includes any compound which breaks down in agrochemical use to form a compound of formula (I).

Examples of the compounds of the invention are shown in Table I below in which the different values for $R^1$ and $R^2$ in the general formula (1) above are presented, and in which the group $R^3$ in the general formula (I) is:

and the value of X is indicated in Table I.

TABLE I

| Compound No. | $R_1$ | $R_2$ | X | M.pt. (°C.) | Comments |
|---|---|---|---|---|---|
| 1 | $-CH_2CH_2CH_2CH_3$ | H | H | 32–35 | |
| 2 | $-CH_2CH_2CH_2CH_3$ | $CH_3$ | H | Oil | |
| 3 | $-CH_2CH_2CH_2CH_2CH_3$ | H | H | 76–78 | |
| 4 | $-CH_2CH_2CH_2CH_2CH_2CH_3$ | H | H | Oil | |
| 5 | $-C(CH_3)_3$ | H | H | 114.5–118.2 | |
| 6 | $-CH(CH_3)CH_2CH_3$ | H | H | 59.1–63.8 | |
| 7 | $-CH_2CH(CH_3)_2$ | H | H | 47.4–50.2 | |
| 8 | $-CH_2CH_2CH(CH_3)_2$ | H | H | 46–48.5 | |
| 9 | $-CH(CH_3)CH_2CH_2CH_3$ | H | H | low melting solid | 1:1 mixture of isomers |
| 10 | $-CH_2CH(CH_3)CH_2CH_3$ | H | H | Oil | |
| 11 | $-CH_2-CH_2-CH_3$ | H | H | 36–39 | |
| 12 | $-CH_2-CH_2-CH_3$ | $CH_3$ | H | Oil | |
| 13 | $-CH_2-CH_2-CH_2-Cl$ | H | H | 61–64 | |
| 14 | $-CH_2-CH_2-Cl$ | H | H | 91–92.5 | |
| 15 | $-CH_2-CHCl-CH_3$ | H | H | 53.5–57 | |
| 16 | 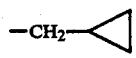 | H | H | 64.1–66.2 | |
| 17 | $-CH_2-CH_2-CH_2-CH_3$ | H | F | gum | |
| 18 | $-CH_2-CH_2-CH_3$ | H | F | gum | |
| 19 | $-CH_2-CH_2-CH_3$ | H | Cl | 67–69 | |
| 20 | $-CH_2-CH_2-CH_2-CH_2-CH_3$ | H | F | oil | |
| 21 | $-CH_2-CH_2-CH_2-CH_2-CH_2-CH_3$ | H | F | oil | |

The compounds of general formula (I) wherein R² is H may be prepared by reacting a compound of general formula (IIIa) or (IIIb)

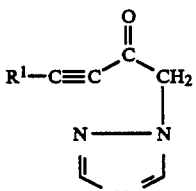 (IIIa)

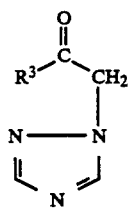 (IIIb)

wherein R¹ and R³ are as defined above, with an organometallic compound which may be represented by the general formula (IVa) or (IVb) respectively.

 (IVa)

 (IVb)

wherein R¹ and R³ are as defined above and M is a metal which is preferably lithium, magnesium, titanium or zirconium. The reaction conveniently takes place in a solvent such as diethyl ether, tetrahydrofuran or dichloromethane at −80° C. to +80° C. in an inert atmosphere. The product is worked up by quenching with a proton donor. When M is magnesium the organometallic compound is more specifically R¹—C≡C—Mg halogen or R³Mg halogen. When M is titanium the organometallic compound is more specifically R¹—C≡C—Ti(O—alkyl)₃ or tBuTi(O—alkyl)₃. When M is zirconium the organometallic compound is more specifically R¹—C≡C—Zr(P—alkyl)₃ or tBuZr(O—alkyl)₃.

The compound of general formula (I) wherein R² is H may also be prepared by reacting a compound of general formula (V) or (VI):

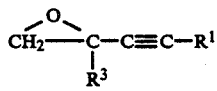 (V)

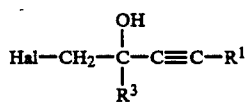 (VI)

in which R¹ and R³ are as defined above and Hal is a halogen atom (preferably a chlorine or bromine atom), with 1,2,4-triazole either in the presence of an acid-binding agent or in the form of one of its alkali metal salts in a convenient solvent.

Suitably the compound of general formula (V) or (VI) is reacted at 20°-100° C. with the sodium salt of 1,2,4-triazole (the salt can typically be prepared by adding either sodium hydride or sodium methoxide to 1,2,4-triazole in a convenient solvent such as acetonitrile, methanol, ethanol or dimethylformamide). The product can be isolated by pouring the reaction mixture into water and extracting the product with a suitable organic solvent e.g. diethyl ether, ethyl acetate or dichloromethane.

The ethers (wherein R² is alkyl) and the esters of the invention are made from the hydroxy compounds by reacting them with the appropriate halide, acid chloride or acid anhydride in the presence of a suitable base.

The compounds of general formula (IIIa), (IIIb), (V) and (VI) can be prepared using conventional methods.

For example compounds of the general formula (V) and (VI) may also be prepared by reacting a compound. of general formula (VIIa) or (VIIb):

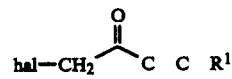 (VIIa)

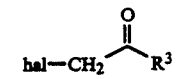 (VIIb)

wherein R¹, R³ and hal are as defined above, with an organometallic compound of general formula (IVa) or (IVb).

Compounds of general formula (IIIa) and (IIIb) may be prepared by reacting a compound of general formula (VIIa) and (VIIb) in which R¹, R³ and Hal are as defined above with 1,2,4-triazole either in the presence of an acid binding agent or in the form of one of its alkali metal salts in a convenient solvent. Compounds of formula (IIIb) wherein R³ is halo tertiary butyl may be prepared by methods set out in the literature, for example DE Nos. 2820361 and 3025242.

A compound of general formula (I) wherein R¹ is halo alkyl may be prepared as described above, for example by the addition of an organometallic reagent such as (IVb) wherein R¹ is haloalkyl to a compound of general formula (IIIb). Alternatively such a compound may be prepared by the addition of an organometallic reagent such as (IVb) wherein R¹ is hydroxylalkyl or a derivative of hydroxyalkyl in which the hydroxyl group is protected for example as an ether, such as tert-butyldimethylsilyl ether or tetrahydropyranyl ether or as an ester, for example the paratoluene sulphonate.

The hydroxyl group or its derivative may then be transformed by one or more steps as set out in the literature into the required haloalkyl compound.

A compound of general formula (I) wherein R¹ is defined as above may also be prepared by treatment of the di-metal salt of a precursor of a compound of the general formula (I) having hydrogen in place of R¹, with an appropriate derivative of the group R¹ for example a halide or a sulphonate.

Suitably the compound of general formula (I) having hydrogen in place of R¹ is reacted at −80° C. to +80° C. with at least two equivalents of a suitable base such as lithium amide in a convenient solvent such as liquid ammonia or tetrahydrofuran to form the di-metal salt. The dimeta salt is then reacted with a suitable halide (for example R¹Cl) at −80° C. to +80° C. The product can be isolated by pouring the reaction mixture into water and extracting with a suitable organic solvent.

The compounds of general formula (V11) may be made using standard methods set out in the literature.

The plant growth regulating effects of the compounds are manifested as, for example, by a stunting or dwarfing effect on the vegetative growth of woody and herbaceous mono- and di-cotyledonous plants. Such stunting or dwarfing may be useful, for example, in peanuts, cereals such as wheat and barley oil seed rape, field beans, sunflowers, potatoes and soya bean where reduction in stem height, with or without further advantageous effects such as stem strengthening, thickening and shortening, internode shortening, increased buttress root formation and more erect stem and leaf orientation, may reduce the risk of lodging and may also permit increased amounts of fertiliser to be applied. The stunting of woody species is useful in controlling the growth of undergrowth under power lines etc. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting. Growth retardation of grasses can help maintenance of grass swards. Examples of suitable grasses are *Stenotaphrum secundatum* (St. Augustine grass), *Cynosurus cristatus, Lolium multiflorum* and *perenne, Agrostis tenuis, Cynodon dactylon* (Bermuda grass), *Dactylis glomerata, Festuca* spp. (e.g. *Festuca rubra*) and Poa spp. (e.g. *Poa pratense*). The compounds may stunt grasses without significant phytotoxic effects and without deleteriously affecting the appearance (particularly the colour) of the grass; this makes such compounds attractive for use on ornamental lawns and on grass verges. They may also have an effect on flower head emergence in, for example, grasses. The compounds can also stunt weed species present in the grasses; examples of such weed species are sedges (e.g. Cyperus spp.) and dicotyledonous weeds (e.g. daisy, plantain, knotweed, speedwell, thistle, docks and ragwort). The growth of non-crop vegetation (e.g. weeds or cover vegetation) can be retarded thus assisting in the maintenance of plantation and field crops. In fruit orchards, particularly orchards subject to soil erosion, the presence of grass cover is important. However excessive grass growth requires substantial maintenance. The compounds of the invention could be useful in this situation as they could restrict growth without killing the plants which would lead to soil erosion; at the same time the degree of competition for nutrients and water by the grass would be reduced and this could result in an increased yield of fruit. In some cases, one grass species may be stunted more than another grass species; this selectivity could be useful, for example, for improving the quality of a sward by preferential suppression of the growth of undesirable species.

The dwarfing may also be useful in miniaturizing ornamental, household, garden and nursery plants (e.g. poinsettias, chrysanthemums, carnations, tulips and daffodils).

As indicated above, the compounds can also be used to stunt woody species. This property can be used to control hedgerows or to shape or reduce the need for pruning, of fruit trees (e.g. apples, pears, cherries, peaches, vines etc).

The plant growth regulating effect may (as implied above) manifest itself in an increase in crop yield; or in an ability in orchards and other crops to increase fruit set, pod set and grain set. Some coniferous trees are not significantly stunted by the compounds so the compounds could be useful in controlling undesirable vegetation in conifer nurseries.

In the potato, vine control in the field and inhibition of sprouting in the store may be possible.

In addition the compounds may be useful as abscision agents resulting in thinning of fruit on the tree and an increase in fruit quality.

Other plant growth regulating effects caused by the compounds include alteration of leaf angle and changes in leaf morphology (both of which may permit increased light interception and utilization) and promotion of tillering in monocotyledonous plants. Improved light interception is of value in all major world crops, e.g. wheat, barley, rice, maize, soya, sugarbeet, potatoes, plantation crops and orchard crops. The leaf angle effect may be useful for example in altering the leaf orientation of, for example, potato crops thereby letting more light into the crops and inducing an increase in photosynthesis and tuber weight. By increasing tillering in monocotyledonous crops (e.g. rice), the number of flowering shoots per unit area may be increased thereby increasing the overall grain yield of such crops. In addition better control and modification of hierarchical relationships is possible both in vegetative and reproductive stages of monocotyledonous and dicotyledonous plant growth, especially in cereals such as wheat, barley, rice and maize, whereby the number of flowering shoots per unit area may be increased and the size distribution of grains within the ear may be modified in such a way as to increase yield. In the treatment of rice plants, or rice crops the invention compounds can be applied, e.g. as granules or a granular formulation, for example as slow release granules, to nursery boxes, paddy water and other like cultivation loci and media. In grass swards, especially amenity grass, an increase in tillering could lead to a denser sward which may result in increased resilience in wear; and to increased yields and better quality of forage grass, e.g. improved digestability and palatability.

The treatment of plants with the compounds can lead to the leaves developing a darker green colour. In dicotyledonous plants such as soyabean and cotton, there may be promotion of sideshooting.

The compounds may inhibit, or at least delay, the flowering of sugar beet (and thereby may increase sugar yield) or otherwise modify the flowering patterns in many other crops. They may also reduce the size of sugar beet without reducing significantly the sugar yield thereby enabling an increase in planting density to be made. Similarly in other root crops (e.g. turnip, swede, mangold, parsnip, beetroot, yam and cassava) it may be possible to increase the planting density.

The compounds could be useful in restricting the vegetative growth of cotton thereby leading to an increase in cotton yield. Crop yields may also be increased by improvement of the harvest index (ie. the harvested yield as a proportion of the total dry matter produced) by altering dry matter partitioning. This applies to all the aforementioned root, pod, cereal, tree, plantation and orchard crops.

The compounds may be useful in rendering plants resistant to stress since the compounds can delay the emergence of plants grown from seed, shorten stem height and delay flowering; these properties could be useful in preventing frost damage in countries where there is significant snow cover in the winter since then the treated plants would remain below snow cover during the cold weather. Further the compounds may cause drought or cold resistance in certain plants.

When applied as seed treatments at low rates the compounds can have a growth stimulating effect on plants.

It is to be understood that not all the compounds of the present invention will necessarily show all the above mentioned plant growth regulating effects. Thus whilst there may be advantages in compounds which have a broad spectrum of plant growth regulating effects against a wide range of species, compounds having a high specific activity with respect to a Particular species and/or plant growth regulating effect may also be of great benefit.

The Examples show that the compounds of the present invention are generally very effective broad species spectrum retardants and also show a substantial greening effect combined with only slight apical damage, even at higher rates of application. In cereals, the compounds generally show excellent reduction of interligular length, which is an indication of internode reduction in mature plants and consequent limitation of the susceptibility of the plants to lodging. The compounds of the present invention are also generally active as retardants on woody species such as apples and vines, providing scope for their use as field management aids. The compounds generally have a substantial green-up effect associated with the activity, and in cereals can influence the tillering which may lead to increased ear number at maturity and hence increases in yield.

The comparisons carried out of compounds of the present invention with compounds of EP No. 0052424 showed that the compounds of Table 1 are clearly superior plant growth regulators across a broad spectrum of species.

Certain of the compounds of the present invention show a more specific mode of action. Thus for example Compound No 1 in Example 15, is considerably more active as a cereal retardant on barley and rice than as a woody species retardant on apples at the 1000 ppm rate.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. With the use of biodegradable polymeric slow release granules rates of 1 to 10 g per hectare are feasible; whilst electrodynamic spraying techniques may also deploy lower rates of application. However, on certain plants even application rates within these ranges may give undesired phytotoxic effects. Routine tests may be necessary to determine the best rate of application of a specific compound for any specific purpose for which it is suitable.

The compounds may be used as such for plant growth regulating purposes but are more conveniently formulated into compositions for such usage. The invention thus provides a plant growth regulating composition comprising a compound of general formula (I) as hereinbefore defined, or a salt or metal complex thereof; and, optionally, a carrier or diluent.

The invention also provides a method of regulating plant growth, which comprises applying to the plant, to seed of a plant or to the locus of a plant or seed, a compound, or a salt or metal complex thereof, as hereinbefore defined, or a composition combining the same.

The compounds, salts, metal complexes, ethers and esters can be applied in a number of ways, for example they can be applied, formulated or unformulaed, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour; or as slow release granules. Application can be to any part of the plant, bush or tree, for example to the foliage, stems, branches or roots, or to soil surrounding the roots, or to the seed before it is planted; or to the soil generally, to paddy water or to hydroponic culture systems. The invention compounds may also be injected into plants or trees and they may also be sprayed onto vegetation using electrodynamic spraying techniques.

The term "plant" as used herein includes seedlings, bushes and trees.

The compounds are preferably used for agricultural and horticultural Purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a micro-encapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The compounds can be used as mixtures with fertilizers (eg nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising the compound of general formula (I) or a salt or metal complex thereof.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s); or which are spray formulations of the kind suitable for use in electrodynamic spraying techniques. The foregoing agents can be cationic, anionic or non-ionic agents. Suitable cationic agents are quaternary ammonium compounds, for example cetyltrimethyl-ammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butyl-naphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), and the concentrate is to be diluted with water before use. These concentrates often should be able to withstand storage for prolonged periods and after such storage be capable of dilution with water in order to form aqueous preparations which remain homogeneous for a sufficient time to enable them to be applied by conventional and electrodynamic spray equipment. The concentrates may conveniently contain up to 95%, suitably 10–85%, for example 25–60%, by weight of the active ingredient(s). These concentrates suitably contain organic acids (e.g. alkaryl or aryl sulphonic acids such as xylenesulphonic acid or dodecyl benzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% to 10%, or 0.01% to 10%, by weight of active ingredient(s) may be used.

The compositions of this invention can comprise also one or more additional compound(s) having biological activity, e.g. compounds having similar or complementary fungicidal or plant growth activity or compounds having plant growth regulating, herbicidal or insecticidal activity.

The additional fungicidal compound can be, for example, one which is capable of combating ear diseases of cereals (e.g. wheat) such as Septoria, Gibberella and Helminthosporium spp., seed and soil borne diseases and downy and powdery mildews on grapes and powdery mildew and scab on apple etc. Examples of suitable additional fungicidal compound are imazalil, benomyl, carbendazim, thiophanate-methyl, captafol, captan, sulphur, triforine, dodemorph, tridemorph, pyrazophos, furalaxyl, ethirimol, tecnazene, dimethirimol, bupirimate, chlorothalonil, vinclozolin, procymidone, iprodione, metalaxyl, forsetyl-aluminium, carboxin, oxycarboxin, fenarimol, nuarimol, fenfuram, methfuroxan, nitrotal-isopropyl, triadimefon, thiabendazole, etridiazole, triadimenol, biloxazol, dithianon, binapacryl, quinomethionate, guazatine, dodine fentin acetate, fentin hydroxide, dinocap, folpet, dichlofluanid, ditalimphos, kitazin, cycloheximide, dichlobutrazol, a dithiocarbamate, a copper compound, a mercury compound, 1-(2-cyano-2-methoxyiminoacetyl)-3-ethyl urea, fenaponil, ofurace, propiconazole, etaconazole and fenpropemorph and fenpropidine.

The compounds of general formula (I) can be mixed with soil, peat or other rooting media for the protection of plants against seed-borne, soil-borne or foliar fungal diseases.

Suitable additional insecticides are Pirimor, Croneton, dimeth- oate, Metasystox, pyrethroid insecticides and formothion.

The other, additional, plant growth regulating compound can be one which controls weeds or seedhead formation, improves the level or longevity of the plant growth regulating activity of the compounds of general formula (I), selectively controls the growth of the less desirable plants (e.g. grasses) or causes the compound of general formula (I) to act faster or slower as a plant growth regulating agent. Some of these other agents will also be herbicides.

Examples of suitable plant growth regulating compounds, which can display synergy in admixture, or use, with the invention compounds are the gibberellins (e.g. $GA_3$, $GA_4$ or $GA_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acids (e.g. triiodobenzoic acid), morphactins (e.g. chlorfluorecol), maleic hydrazide, glyphosate, glyphosine, long chain fatty alcohols and acids, dikegulac, fluoridamid, mefluidide, substituted quaternary ammonium and phosphonium compounds (e.g. chlormequat* chlorphonium or mepiquat chloride*), ethephon, carbetamide, methyl-3,6-dichloroanisate, daminozide*, asulam, abscisic acid, isopyrimol, 1-(4-chlorophenyl)-4,6-dimethyl-2-oxo-1,2-dihydropyridine-3-carboxylic acid, hydroxybenzonitriles (e.g. bromoxynil), difenzoquat*, benzoylprop-ethyl 3,6-dichloropicolinic acid, fenpentezol, triapenthanol, flurpirimidol, paclobutrazol, tetcyclacis and tecnazene. Synergy will be most likely to occur with those of the foregoing which are quaternary ammonium compounds and with those marked with an asterisk.

For certain applications, for example in the injection to the compounds of the invention into trees or plants, it is desirable that the compounds have a relatively high solubility in water, for example a solubility in excess of 30 parts per million. Thus Compound No. 1 of Table I for example has a solubility in water of 1900 parts per million and is very suitable for this application. The compounds may alternatively be injected into the tree in the form of an organic solution, for example a solution in a lower alcohol.

For certain applications it is also desirable that the compound has a low persistancy in soil to prevent carry-over to adjacent crops or even crops planted subsequently in the same soil. Preferably the compound for use in such applications has a half life in the soil of less than 20 weeks. Thus Compound No. 1 of Table I for example has a half life in the soil of only 1 to 2 weeks and is very suitable for applications in which low soil persistency is desirable.

The invention is illustrated by the following Examples.

EXAMPLE 1

This Example illustrates the preparation of Compound 1 of Table I -2,2-dimethyl-3-hydroxy-3-(hex-1-yne-1-yl)-4-(1,2,4-triazol-1-yl)-butane.

To a solution of ethyl magnesium bromide [made from ethyl bromide (3.95 g, 0.036M) and magnesium (1.27 g, 0.053 g.atoms) in dry diethyl ether (20 mls) at 20° C. under Argon was added gradually hex-1-yne (3.65 g, 0.045M). The resulting mixture was heated at reflux for 1 hour then cooled to 5° C. To this mixture was added dropwise a solution of 2,2-dimethyl-4-(1,2,4-triazol-1-yl)butane-3-one (5.5 g, 0.033M) in dry dichloromethane (120 mls). The resulting mixture was left to stir at 20° C. for ¾ hours and aqueous ammonium chloride (100 ml, 10%) then added. The organic layer was separated, washed with water and dried (anhydrous MgSO$_4$). Concentration in vacuo gave a pale yellow oil. Chromatography on silica using diethyl ether as eluant gave the title compound (5.05 g) as a pale yellow oil. Distillation (b.pt 180°-210° C. 0.4mmHg) gave a very pale yellow oil which gave almost white crystals (melting point 32°-35° C.) on standing.

NMR (CDCl$_3$) 0.70-1.00 (3H, cmplx), 1.13 (9H,s), 1.00-1.50 4H (cmplx), 1.90-2.20 (2H,cmplx), 4.10-4.50 (3H,cmplx), 7.90 (1H,s), 8.24 (1H,s).

IR (nujol) 3500-3000 (medium), 3148 (medium) 2230 (weak).

m/e MH+250; 192, 167, 83.

Analysis C$_{14}$H$_{23}$N$_3$O requires C, 67.42; H, 9.30; N, 16.86%. found C, 67.37; H, 9.66; N 16.87%.

EXAMPLE 2

This Example illustrates the preparation of compound 3 of Table I -2,2-dimethyl-3-hydroxy-3-(hept-1-yne-1-yl)-4-(1,2,4-triazol-1-yl)-butane.

To a solution of hept-1-yne (3.9 g, 0.041 mol) in dry tetrahydrofuran (30 mls) at −70° C. under nitrogen was added n-butyllithium (30 mls of a 1.55M solution in hexane) and the resulting mixture stirred for 1 hour. To this mixture was added a solution of 2,2-dimethyl-4-(1,2,4-triazol-1-yl)-butan-3-one (6.8 g, 0.041 mol) in dry tetrahydrofuran (50 ml), and the resulting mixture was allowed to warm to room temperature. The reaction mixture was partitioned between ethyl acetate and aqueous HCl (1.0M). The aqueous was further extracted with ethyl acetate. The combined ethyl acetate extracts were washed with water, saturated sodium bicarbonate solution and brine, dried (anhydrous MgSO$_4$) and then concentrated in vacuo to give a yellow oil. Chromatography on silica using gradient elution (diethyl ether 20-80% in petrol) gave the title compound (2.87 g) as a yellow crystalline solid (melting point 76°-78° C.).

NMR (CDCl$_3$) 0.70-1.00 (3H,cmplx), 1.10-1.50 (15H,complx) 1.80-2.10 (2H,cmplx), 3.75 (1H,s) 4.30 (2H,s), 7.95 (1H,s), 8.18 (1H,s).

IR (nujol) 3080-3600 (strong), 3130, 2250 cm$^{-1}$.

m/e no M+, 248, 206, 181, 82.

Analysis C$_{15}$H$_{25}$N$_3$O requires: C, 68.40, H, 9.57; N, 15.95%. found: C, 68.38; H, 9.43, N, 15.90%.

EXAMPLE 3

This Example illustrates the preparation of Compound No 8 of Table I -2,2-dimethyl-3-hydroxy-3-(5-methyl-hex-1- yne-1-yl)-4-(1,2,4-triazol-1-yl)-butane.

To a solution of ethyl magnesium bromide [made from ethyl bromide (3.95 g, 0.036M) and magnesium (1.27 g, 0.053 g. at)] in dry diethyl ether (30 mls) at 20° C. under Argon was added 5-methylhex-1-yne (3.64 g, 0.038M). The resulting mixture was heated at reflux for 1 hour then cooled to 5° C. To this mixture was added dropwise a solution of 2,2-dimethyl-4-(1,2,4-triazol-1-yl)butane-3-one (5.5 g, 0.033M) in dichloromethane (100 mls). The resulting mixture was left to stir at 20° C. for 1 hour. Tetrahydrofuran (50 mls) and then aqueous ammonium chloride were added. More water and diethyl ether were added and the organic layer was separated. The aqueous layer was re-extracted with diethyl ether. The combined organic layers were washed with water, dried (anhydrous MgSO$_4$) and concentrated in vacuo to give a yellow oil. Chromatography on silica using diethyl ether as eluant gave the title compound (3.62 g) as a white fluffy solid (melting point 46°-48° C.).

NMR (CDCl$_3$) 0.76 (6H,d), 1.06 (9H,s), 1.05-1.60 (3H,cmplx), 1.95 (2H,t), 3.90-4.10 (1H, broad s), 4.14 (2H,s), 7.84 (1H,s), 8.12 (1H,s).

IR (nujol) 3600-3050 (medium), 3130 (medium-weak), 2242 (weak) cm$^{31\ 1}$.

m/e No M+, 248, 206, 83.

Analysis C$_{15}$H$_{25}$N$_3$O requires: C, 68.40; H, 9.57; N, 15.95%. found: C, 68.37; H, 9.42; N, 14.84%.

EXAMPLE 4

Compound No. 4 of Table I -2,2-dimethyl-3-hydroxy-3-(oct-1-yne-1-yl)-4-(1,2,4-triazol-1-yl)-butane was prepared using the general method of Example 7 and was characterised as follows:

NMR (CDCl$_3$) 0.70-11.50 (20H,cmplx), 1.82-2.12 (2H, cmplx), 3.73 (1H,s), 4.33 (2H,s), 7.95 (1H,s), 8.19 (1H,s).

IR (film) 3160-3600, 3120, 2220 cm$^{-1}$.

m/e No M+, 262, 220, 195, 82, 57.

Boiling point: (Kugelrohr) 215°-230° C. at 0.25 mmHg.

Analysis C$_{16}$H$_{27}$N$_3$O requires: C, 69.28; H, 9.81; N, 15.15%. found: Cm 69.48; H, 9.68; N, 13.46%.

EXAMPLE 5

Compound No. 5 of Table I -2,2-dimethyl-3-hydroxy-3-(3,3-dimethyl-but-1-yne-1-yl)-4-(1,2,4-triazol-1-yl)-butane was prepared using the general mehod of Example 7 and was characterised as follows:

NMR (CDCl$_3$) 1.07 (9H,s), 1.14 (9H,s), 3.81 (1H,s), 4.32 (2H,s), 7.96 (1H,s), 8.20 (1H,s).

IR (nujol) 3070-3500, 3150 (weak), 2230 (weak) cm$^{-1}$.

m/e No M+, 234, 192, 123, 70.

Analysis $C_{14}H_{23}N_3O$ requires: C, 67.44; H, 9.30; N, 16.85%, found: C, 67.26; H, 9.31; N, 16.36%.

Melting point 114.5°–118.2° C.

EXAMPLE 6

Compound No. 6 of Table I -2,2-dimethyl-3-hydroxy-3-(3-methyl-pent-1-yne-1-yl)-4-(1,2,4-triazol-1-yl)-butane was prepared as follows:

To a solution of ethyl magnesium bromide (20 ml of a 3M solution in ether) in dry diethyl ether (30 ml) under $N_2$ at room temperature was added a solution of 3-methyl-1pentyne (5 g, 0.06 mol) in diethyl ether (20 ml). The resulting mixture was heated under reflux for 1 hour, and then cooled to 0° C. To this mixture was added slowly a solution of 2,2-dimethyl-4-(1,2,4-triazol-1-yl)-butane-3-one (8.4 g, 0.05 mol) in dry dichloromethane (150 ml), and the mixture stirred for 45 minutes, a gelatinous precipitate formed. Ammonium chloride solution was added to the mixture, and the organic layer separated and washed with water and brine, dried over $MgSO_4$ and concentrated in vacuo. The residue was chromatographed on silica eluting with diethyl ether (20–100%) in petrol gave 2,2-dimethyl-3-hydroxy-3-(3-methyl-pent-1-yne-1-yl)-4-(1,2,4-triazol-1-yl)-butane) as a white solid (4.29 g) (mpt=59°–64° C.).

NMR ($CDCl_3$) 0.65–1.45, (17H, cmplx), 1.91–2.32, (1H,cmplx), 3.73 (1H,s), 4.33 (2H,s), 7.96 (1H,s), 8.20 (1H,s).

IR (film) 3050–3600 (strong), 2230 $cm^{-1}$.

m/e No M+, 234, 192, 167, 82

Analysis $C_{14}H_{23}N_3O$ Requires: C, 67.44; H, 9.30; N, 16.85%. Found: C, 67.12; H, 9.14; N, 16.67%.

Melting point 59.1°–63.8° C.

EXAMPLE 7

This Example illustrates the preparation of Compound No. 7 of Table I -2,2-dimethyl-3-hydroxy-3-(4-methyl-pent-1-yne-1-yl)-4-(1,2,4-triazol-1-yl)-butane.

To a solution of 4-methylpent-1-yne (2.5 g, 0.03 mol) in dry tetrahydrofuran (35 ml) under nitrogen at −70° C. was added n-butyl lithium (19 ml of a 1.55M solution in hexane. The resulting mixture was stirred for 20 minutes, then chloro- titanium tri-isopropoxide (7.2 ml, 0.03 mol) was added. After a further 20 minutes, a solution of 2,2-dimethyl-4- (1,2,4-triazol-1-yl)-butan-3-one (5.0 g, 0.03 mol) in dry dichloromethane (30 ml) was added to the reaction mixture, which was then allowed to warm to room temperature and stirred for 3 hours. To the reaction mixture was added ethyl acetate and saturated ammonium chloride solution, and the whole mixture was filtered through "Hyflo" to remove the gelatinous yellow precipitate. The organic portion of the filtrate was washed with water and brine, dried (anhydrous $MgSO_4$) and concentrated in vacuo to give the crude product Chromatography on silica using gradient elution (diethyl ether 20–100% in petrol) gave the title compound (4.78 g) as a pale yellow solid (melting point 47.4°–50.2° C.).

NMR ($CDCl_3$) 0.80 (6H,d), 1.12 (9H,s), 1.30–2.00 (3H, cmplx), 3.72 (1H,s), 4.31 (2H,s), 7.94 (1H,s), 8.18 (1H,s).

IR (nujol) 3150–3450, 3130, 2230 $cm^{-1}$.

m/e No m+, 234, 192, 167, 123, 82.

Analysis: $C_{14}H_{23}N_3O$ requires C, 67.46; H, 9.24; N, 16.87%. found: C, 67.31; H, 9.74; N, 16.85%.

EXAMPLE 8

Compound No. 9 of Table I -2,2-dimethyl-3-hydroxy-3-(3-methyl-hex-1-yne-1-yl)-4-(1,2,4-triazol-1-yl)-butane was prepared using the general method of Example 7 and was found to be a white, low melting solid comprising a mixture of diastereoisomers characterised as follows NMR ($CDCl_3$) 0.74–1.55 (19H, cmplx), 1.80–2.40 (1H,cmplx), 4.04 (1H, broad d), 4.36 (2H,s), 7.96 (1H,s), 8.24 (1H,s).

IR (Film) 3030–3600 (strong), 2230 $cm^{-1}$.

m/e No M+, 248, 206, 181, 82.

EXAMPLE 9

Compound No. 10 of Table I -2,2-dimethyl-3-hydroxy-3-(4-methyl-hex-1-yne-1-yl)-4-(1,2,4-triazol-1-yl)-butane was prepared using the general method of Example 7 and characterised as follows NMR ($CDCl_3$) 0.60–1.60 (18H,cmplx), 1.85–2.04 (2H,cmplx), 4.10 (1H,s), 4.34 (2H,s), 7.92 (1H,s), 8.21 (1H,s).

IR (film) 3050–3600, 2230 $cm^{-1}$.

m/e No M+, 248, 206, 181, 82, 57.

Analysis $C_{15}H_{25}N_3O$ requires: C, 68.40; H, 9.57; N, 15.95%. found: C, 67.68; H, 9.97; N, 16.17%.

Boiling point (Kugelrohr) 240° C. at 0.6 mm Hg.

EXAMPLE 10

Compound No. 11 of Table I -2,2-dimethyl-3-hydroxy-3-pent-1-yne-1-yl)-4-(1,2,4-triazol-1-yl)-butane was prepared using the general method of Example 7 and characterised as follows: White crystals melting point 36°–39° C.

NMR ($CDCl_3$) 0.79 (3H,t), 1.06 (9H,s), 0.90–1.54 (2H, cmplx), 1.96 (2H,t), 4.25 (2H,s), 4.50–5.20 (1H,broad), 7.79 (1H,s), 8.16 (1H,s).

IR (nujol) $cm^{-1}$ 3500–3000 (medium), 3150 (medium), 2245 (weak).

m/e No M+; 220, 178, 83.

EXAMPLE 11

Compound No 12 of Table I was prepared as follows: To a solution of Compound 11, prepared in Example 11 (0.94 g, 0.04M) in dry dimethylformamid,e (10 mls) was added Portion wise sodium hydride (50%, 0.196 g, 0.004m). The reaction mixture was stirred at room temperature for 20 minutes then methyl iodide (0.568 g, 0.004 m) was added dropwise. The resultant mixture was heated at 80° C. for 4 hours then cooled and the dimethylformamide removed in vacuo. The residue was partitioned between water and ether. The ether layer was removed and the aqueous layer further extracted with ether. The combined ethereal extracts were washed with brine, dried (anhydrous $MgSo_4$) and evaporated to give a brown oil. Chromatography on silica using gradient elution (ether 0–100% in petrol) to give the title compound (0.708 g) as an orange oil.

NMR ($CDCl_3$) 0.96 (3H,t J8 Hz), 1.06 (9H,s), 1.5 (1H, hextet J8 Hz), 2.22 (2H,t J8 Hz), 3.21 (3H, s), 4.38 (2H,s), 7.93 (1H,s), 8.23 (1H,s). IR (liquid film) 2230 $cm^{-1}$.

m/e No M+ 234, 219, 218, 192, 167.

EXAMPLE 12

Compound No 2 of Table 1 was prepared as follows: To a solution of Compound No 1, prepared in Example 1 (1.85 g, 0.00743m) in dry dimethylformamide (10 mls)

was added portion wise sodium hydride (50%, 0.356 g, 0.00743 m). The reaction mixture was stirred for 20 minutes at room temperature. Then methyl iodide (1.054 g, 0.00743 m) was added dropwise. The resultant mixture was heated at 80° C. for 6 hours then cooled and the dimethylformamide in vacuo. The residue was partitioned between water and ether. The ether layer was removed and the aqueous layer further extracted with ether. The combined ethereal extracts were washed with brine, dried (anhydrous $MgSO_4$) and evaporated to give an orange oil. Chromatography on silica using gradient elution (ether 0–100% in petrol) to give the title compound (1.54 g) as a pale yellow oil.

NMR ($CDCl_3$) 0.90 (3H,tJ8 Hz), 1.06 (9H,s), 1.0–1.6 (4H, cmplx), 2.22 (2H,tJ8 Hz), 3.21 (3H,s), 4.37 (2H,s), 7.89 (1H,s), 8.19 (1H,s).

IR (liquid film) 3150, 2240 $cm^{-1}$.

EXAMPLE 13

This Example illustrates the preparation of compound No. 16 of Table I. 2,2-Dimethyl-3-hydroxy-3-(3-cyclopropyl-prop-1-yne-lyl)-4-(1,2,4-triazol-1-yl)-butane.

To a solution of 2,2-dimethyl-3-hydroxy-3-(trimethylsilylacetylinyl)-4-(1,2,4-triazol-1-yl)-butane Prepared using the general method of Example 1 (4.0 g, 0.015 m) in methanol (40 mls) at 20° C. was added anhydrous potassium carbonate (0.25 g, 0.0018M). The resulting mixture was stirred at 20° C. for 18 hours, then concentrated in vacuo to give an off-white residue. This was partitioned between dichloromethane and water and brought to pH7 with acetic acid. The organic layer was separated, washed with water, dried (anhydrous $MgSO_4$) and concentrated in vacuo to give a white solid. Trituration with petroleum ether (30–40) and filtration gave (2,2-dimethyl-3-hydroxy-3-acetylenyl-4-(1,2,4-triazol-1-yl)-butane) as a white fluffy (2.51 g) solid (mp. 133°–134° C.).

To liquid ammonia (approx. 50 ml) at −60° C. was added a small piece of lithium (from 0.32 g, 46 mmol) followed by a spatula tip full of ferric nitrate. The remaining lithium was added gradually and the reaction mixture stirred for 30 minutes until the blue colour had been discharged and a grey suspension was left. To the reaction mixture was added a solution of the product from Stage 1 (3.0 g, 15.5 mmol) in THF (25 ml) and the mixture stirred for 90 minutes, allowing the bath temperature to rise to −40° C. The mixture was cooled to −60° C., cyclopropyl methyl bromide (3 ml, 31 mmol) was added then the reaction mixture was allowed to warm to room temperature overnight. The reaction mixture was partitioned between ethyl acetate and 20% $NH_4Cl$ solution, then the aqueous portion was further extracted with ethyl acetate. The combined organic extracts were washed with water and brine, dried over $MgSO_4$ and concentrated in vacuo to give a yellow oil. Column chromatography on silica gel eluting with diethyl ether 10–100% in petrol gave the title compound as a white solid (2.1 g) (mp. 64.1°–66.2° C.).

IR (nujol) 3600–3050, 3080, 2240, 1510 $cm^{-1}$.

m/e No M+, 232, 190, 165, 121, 82.

Analysis $C_{14}H_{21}N_3O$, requires: C, 67.99; H,8.56; N,16.99%. found C: 68.13; H,8.17; N,17.14%. ($CDCl_3$, 90 MHz) 0.1 (2H,cmplx); 0.4 (2H,cmplx);

NMR ($CDCl_3$, 90 MHz): 0.1 (2H, cmplx); 0.4 (2H, cmplx); 0.7 (1H,cmplx); 1.16 (9H,s); 2.1 (2H,d); 3.76 (1H,s); 4.32 (2H,s); 7.95 (1H,s); 8.2 (1H,s).

EXAMPLE 14

This Example illustrates the preparation of Compound No. 17 Table No. 1, 2,2-dimethyl-1-fluoro-3-hydroxy-3-(hex-1-yne-1-yl)-4-(1,2,4-triazole-1-yl)-butane.

To a stirred solution of hex-1-yne (1.0 g, 11 mmol) in dry THF (30 ml) was added n-butyllithium (4.5 ml of 2.6M, 11.5 mmol) at −78° C. under a nitrogen atmosphere followed by chlorotitanium tri-isopropoxide (11 ml of 1 M, 11 mmol). After 15 minutes, a solution of 3,3-dimethyl-4-fluoro-1-(1,2,4-triazol-1-yl)butan-2-one (prepared as in DE No. 2,820,361) (2.0 g, 11 mmol) in dry THF (15 ml) was added dropwise. Upon complete addition the mixture was allowed to warm to room temperature and stirred for 18 hours. The reaction mixture was then poured onto ice and extracted with ether (2×250 ml). The ethereal solution was washed with saturated brine solution then dried over anhydrous magnesium sulphate and the solvent removed. The resulting yellow oil was chromatographed to give a yellow gum (0.61 g, 21%), bp 220° C. 0.2 mmHg 1.R 3250, 2980, 2240, 1510, 1280, 1200, 1140, 1080, 1020, 890, 740, 680 $cm^{-1}$; NMR (90 MHz; $CDCl_3$) 0.74–0.98 (3H,m); 1.16 (6H,s); 1.23–1.5 (4H,m); 2.06 (2H,t,J=6.3 Hz); 4.38 (2H,s); 4.2 (1H,br); 4.46 (2H,dq,J=47 and 8 Hz); 7.92 (1H,s); 8.12 (1H,s); m/z 268 (M+H+), 192, 185, 83 (100%).

EXAMPLE 15

This Example illustrates the preparation of compound No. 14 of Table I. 2,2-Dimethyl-3-hydroxy-3-(4-chloro-but-1-yne-1-yl)-4-(1,2,4-triazol-1-yl)-butane.

STAGE 1

Preparation of the toluene sulphonate derivative of the title compound

To a solution of 4-toluenesulphonyl-but-1-yne (7.4 g, 33mmol) in dry tetrahydrofuran (30 ml), at −50° C. under nitrogen, was added n-butyllithium (21 ml of a 1.6 molar solution in hexane) and the reaction mixture was stirred for 20 minutes. A solution of chlorotitanium triisopropoxide (33 ml of a 1.0 molar solution in hexane) was added slowly and the mixture stirred for 25 minutes. A solution of triazolyl pinacolone (5.0 g, 30 ml) in tetrahydrofuran (40 ml) was added and the mixture allowed to warm slowly to room temperature. The reaction was quenched with ammonium chloride solution, and extracted with ethyl acetate (x3) The combined organic extracts were washed with water and brine, dried over anhydrous magnesium sulphate and evaporated to dryness to give a yellow oil (11.3 g). Column chromatography of the crude product on silica gel, eluting with ethyl acetate 10–80% in petrol, afforded the toluene sulphonyl derivative as a white crystalline solid (4.3 g) (mp. 90°–92° C.).

STAGE 2

A mixture of the product of Stage 1 (1.0 g, 2.6 mnol) and lithium chloride (0.27 g, 6.4 mmol) in dimethyl sulphoxide (20 ml) was heated at 100° C. (bath temperature) for 3 hours. The reaction mixture was cooled to room temperature and partitioned between ethyl acetate and water. The aqueous portion was further extracted with ethyl acetate, and the combined organic extracts were washed with saturated sodium hydrogen carbonate solution, water and brine, dried over anhydrous magnesium sulphate and evaporated to dryness to give the title compound, as a pale yellow crystalline solid (0.64 g) (mp 91°–92½° C.)

NMR (CDCl$_3$, 90 MHz) 1.1 (9H,s); 2.48 (2H,t); 3.38 (2H,t); 4.04 (1H,broad S); 4.18 (2H,s); 7.90 (1H,s); 8.18 (1H,s).

IR (nujol) 3550–3050, 3170, 2250 cm$^{-1}$.

Analysis C$_{12}$H$_{18}$N$_3$OCl, requires C,56.36; H,7.09; N,16.43; Cl, 13.86%, found C,56.56; H,7.14; N,16.24; Cl, 13.19%.

wheat and barley, which were grown in 16° C. day 13° C. night temperatures

After 2-3 weeks in the glasshouse, depending on the time of year, the plants were visually assessed for morphological characteristics. Formulations blanks were used as controls to assess the Plants. The results are Presented in Table III.

TABLE II

| PLANT MATERIAL USED FOR WHOLE PLANT SCREEN | | | | | |
|---|---|---|---|---|---|
| Species | Code | Variety | Growth Stage at Treatment | No. Plants per 3" Pot | Compost Type |
| Barley | BR | Atem | 1-1.5 leaves | 4 | JIP* or PEAT |
| Wheat | WW | Timmo | 1-1.5 leaves | 4 | JIP OR PEAT |
| Maize | MZ | Earliking | 2¼ leaves | 1 | PEAT |
| Vines | VN | Chanez + unspecified | 4 leaves | 1 | PEAT |
| Soya | SY | Amsoy | 1st trifoliate | 1 | JIP |
| Tomato | TO | Ailsa Craig | 1.5-2 leaves | 1 | PEAT |
| Lettuce | LT | Verpia | 3-4 leaves | 1 | PEAT |
| Sugar beet | SB | Amono | 2 leaves | 1 | PEAT |
| *Agrostis tenius* | AT | | cut to 2 cm | Grown in rows | |
| *Cynosurus cristatus* | CC | | 48 hours before | in plastic | PEAT |
| *Dacrylis glomerata* | DA | | treatment | punnets | |
| Radish | RA | Istar | seeds | 4 | PEAT |

JIP* = John Innes Potting Compost.

TABLE III

| COMPOUND NO. | WW | BR | MZ | AT | CC | DA | SY | SB | TO | VN | RA | LT |
|---|---|---|---|---|---|---|---|---|---|---|---|---|
| 1 | 3T | 3T | 2GA | 3G | 2G | 2G | 1G | 1G | 2G | 1GT | 2G | — |
| 2 | 2G | | 2GA | | 1G | | 3GT | 1G | 1G | — | | 1 |
| 3 | 2GT | 1T | 1G | 2G | 2G | 2G | 3GA | 1G | 2G | 2GAT | 3 | |
| 4 | 1GT | | 1G | | | 1 | 1G | G | 2G | 1G | — | 2 |
| 5 | 2 | | | 1 | 2 | | 2G | | G | 1GT | | 1 |
| 6 | 3GT | 2G | | 1 | 1 | 1 | 2GA | 1G | 1G | 2GT | | 1G |
| 7 | 3GT | 2GT | | 2G | 2G | 1G | 3GAT | 1G | 2GT | GT | — | 1G |
| 8 | 3GT | 1T | 1G | 1G | 2G | 1G | 3G | G | 2G | 1 | 3G | 1G |
| 9 | 2GT | 1 | | 1 | 2 | 2 | 2GAT | G | 2G | 2GT | — | 1 |
| 10 | 2GT | 2GT | | 1 | 2 | 1 | 2GA | G | 1G | | — | G |
| 11 | 1 | | A | | 1 | | G | | | 2T | | |

Key:
Retardation 1-3 where
1 = 10-30% retardation
2 = 21-60% retardation
3 = 61-100% retardation
Greening effect = G
Apical damage = A
Tillering or side shooting = T
Blank means less than 10% effect.
— indicates that the compound was not tested against this species.

EXAMPLE 16

Whole Plant Screen (1)

Compound numbers 1-11 of Table I were tested on the whole plant screen. The use of whole plant in this context refers to entire plants as opposed to a partial screen or an enzyme screen. The compounds were tested for plant growth regulator activity against up to twelve plant species for various growth effects relevant to plant growth regulation.

Methodology

The plant species used in this screen are presented in Table II, with the leaf stage at which they were sprayed. Each chemical was applied at 4000 ppm (4 kg/ha in a 1000 l/ha field volume) using a tracksprayer and a SS8004E (Teejet) nozzle.

After spray, the plants were grown in a glasshouse with 25° C. day/22° C. night temperatures and supplementary lighting was supplied when necessary (from mercury vapour lamps), to provide a 16 hour photoperiod. The exception to this were the temperate cereals,

EXAMPLE 17

Whole Plant Screen (2)

Compound numbers 12-13, 16-17 and 19-20 were tested on an alternative whole plant screen (2). The compounds were tested for plant growth regulator activity against five species for various growth effects relevant to plant growth regulation.

Methodology

The plant species used in this screen are presented in Table IV with the leaf stage at which they were sprayed. Each chemical was applied at 4000 ppm (4 kg/ha in a 1000 l/ha field volume) using a tracksprayer and a SS8004E (Teejet) nozzle.

After spray the plants were grown in a glasshouse with 25° C. day 22° C. night temperatures and supplementary lighting was supplied when necessary (from mercury vapour lamps), to provide a 16 hour photoperiod. The exception to this were the temperate cereals, wheat and barley which were grown in 16° C. day 13° C. night temperatures.

After 2-6 weeks in the glasshouse, depending on the time of year, the plants were visually assessed for morphological characteristics. Formulation blanks were used as controls to assess the plants. The results are presented in Table V.

TABLE IV
PLANT MATERIAL USED FOR WHOLE PLANT SCREEN (2)

| Species | Code | Variety | Growth Stage at Treatment | No. Plants per 3"0 Pot | Compost Type |
|---|---|---|---|---|---|
| Barley | BR | Atem | 1-1.5 leaves | 4 | JIP* |
| Wheat | WW | Timmo | 1-1.5 leaves | 4 | JIP |
| Maize | MZ | Earliking | 2¼ leaves | 1 | PEAT |
| Apple | AP | Red Delicious | 4-5 leaves | 1 | JIP |
| Rice | RC | Ishikari | 2-2½ leaves | 4 | JIP |

JIP* = John Innes Potting Compost.

TABLE V

| SPECIES | COMPOUND NO. | R | G | A | T | I |
|---|---|---|---|---|---|---|
| BR | 13 | 1 | | | | 2 |
| | 16 | 2 | 1 | | | 3 |
| | 17 | 2 | | | | 2 |
| | 20 | 1 | | | | 1 |
| WW | 13 | 1 | 1 | | 1 | 3 |
| | 16 | 2 | | | 1 | 3 |
| | 17 | 2 | 1 | | 1 | 2 |
| | 19* | 1 | | | | 1 |
| | 20 | 2 | 2 | | 2 | 3 |
| RC | 13 | 2 | | | 1 | 2 |
| | 16 | 3 | 2 | | 1 | 3 |
| | 20 | | | | 1 | |
| MZ | 12 | 1 | | | | 1 |
| | 13 | 1 | | | | 1 |
| Ap | 12 | 1 | | | | 1 |
| | 16 | 3 | 2 | 2 | 2 | 3 |
| | 17 | 2 | | 3 | 2 | 2 |

*(1000 ppm)
Key:
R = Retardation
G = Greening effect
A = Apical damage
T = Tillering or side shooting
I = Interligular or internodal length reduction
All effects are scored visually on a 1-3 basis where
1 = 10-30%
2 = 31-60%
3 = 61-100%
Blank means less than 10% effect.

EXAMPLE 18

Intermediate Retardant Test

Methodology

Three species are involved in this test RICE, SPRING-BARLEY and APPLES. The variety and growth stages at spray are outlined in Table VI. Compounds were applied at 1000 ppm and 4000 ppm respectively (1 kg and 4 kg ha$^{-1}$ at a field volume of 1000 l/ha$^{-1}$) as an overall spray. This gives a foliar and root component in the test, i.e. this test will detect the activity of both root and foliar acting compounds. The rice was grown in 4" 'paddy' pots, i.e. the roots and bottom of the stems are immersed in water under conditions corresponding to those in paddy fields. Spring barley and apples were grown in 4" pots. The plants were assessed for height to top-most ligule at approximately 28 days after treatment for spring barley and rice and for height to apex at approximately 28 days after the treatment for apples. The results are presented in Tables VII to IX. In each case the result for the 1000 ppm and 4000 ppm test for each compound is compared to the height of the formulation blank in that test, presented as a percentage reduction in height compared to the formulation blank. A blank indicates that the compound was substantially inactive as a retardant at that particular rate of application.

TABLE VI
PLANT MATERIAL FOR INTERMEDIATE RETARDANT TEST

| Species | Variety | Growth Stage at Treatment | No. Plants per 4" Pot | Compost Type |
|---|---|---|---|---|
| Spring Barley | Atem/kym | 3 leaves | 4 | JIP 1 |
| Rice | Ishikari | 3-4 leaves | 2 | SM2:JIP 1 |
| Apples | Red Delicious | 5-10 cm high | 1 | SM2:JIP 1 |

JIP 1 = John Innes Potting Compost.
SM2 = a mixture of loam and grit.

TABLE VII
Percentage Reduction in Height of Rice.
(Compared to formulation blank).

| | Rate | |
|---|---|---|
| COMPOUND NO. | 1000 ppm | 4000 ppm |
| 1 | 24.6 | 49.9 |
| 2 | 17.4 | 34.6 |
| 3 | 21.2 | 40.8 |
| 4 | | 5.8 |
| 5 | 11.4 | 21.2 |
| 6 | 11.2 | 22.7 |
| 7 | 11.1 | 26.0 |
| 8 | 26.6 | 47.7 |
| 9 | 8.2 | 32.0 |
| 10 | 20.7 | 38.2 |
| 12 | 23.8 | 49.7 |
| 13 | 6.0 | 5.2 |
| 16 | 14.0 | 34.0 |
| 17 | | 22.0 |
| 19 | | |

TABLE VIII
Percentage Reduction in Height of Spring Barley.
(Compared to formulation blank).

| | Rate | |
|---|---|---|
| COMPOUND NO. | 1000 ppm | 4000 ppm |
| 1 | 32.3 | 60.7 |
| 2 | 0.2 | 25.6 |
| 3 | 18.5 | 34.7 |
| 4 | 23.7 | 27.5 |
| 5 | 7.0 | 22.6 |
| 6 | 0.8 | 23.5 |
| 7 | 33.0 | 75.4 |
| 8 | 39.6 | 65.8 |
| 9 | 15.7 | 32.9 |
| 10 | 20.2 | 72.4 |
| 11 | 24.0 | 49.4 |
| 12 | 2.7 | 12.6 |
| 13 | 17.0 | 41.0 |
| 16 | 11.0 | 24.0 |
| 17 | | 24.0 |
| 19 | | |

TABLE IX
Percentage Reduction in Height of Apples.
(Compared to formulation blank).

| | Rate | |
|---|---|---|
| COMPOUND NO. | 1000 ppm | 4000 ppm |
| 1 | | 51.6 |
| 2 | | 12.3 |
| 3 | 9.5 | 25.9 |
| 4 | 8.2 | 21.0 |
| 5 | | 31.5 |
| 6 | 1.2 | 38.6 |
| 7 | 15.0 | 31.0 |
| 8 | 7.5 | 26.0 |

TABLE IX-continued

Percentage Reduction in Height of Apples.
(Compared to formulation blank).

| COMPOUND NO. | Rate 1000 ppm | 4000 ppm |
|---|---|---|
| 9 |  | 10.8 |
| 10 | 9.8 | 27.1 |
| 11 |  |  |
| 12 | 15.7 | 33.6 |
| 13 | 2.8 | 9.2 |
| 16 | 31.8 | 62.8 |
| 17 | 9.9 | 54.5 |
| 19 | — | 36.6 |
| 21 | 10.0 | 0 |

The following Example is a general indicative comparison of compounds from EP No. 0052424 with compounds from the preferred class in the present invention. The compounds have not been side-by-side tested on this Example because of the large numbers involved but the retardant activity can be compared using a standard which has been on each test.

EXAMPLE 19

The compounds which are compared in this Example have been tested on one of two tests. These are the Whole Plant Screen (1) and Whole Plant Screen (2) the methods for which are described in Examples 17 and 18 respectively.

An across screen comparison between compounds is made by expressing the total retardation (ie. sum of retardation scores recorded for each species tested) caused by the compound as a percentage of the total retardation caused by the standard in that test. The standard chemical gives a measure of the performance of the test and environmental factors. By expressing the test compound activity as a percentage of the standard compound activity these factors can be eliminated. The same standard has been used in every test and this is paclobutrazol a proprietory growth regulator. The results are presented in Tables X and XI.

Whilst the present example demonstrates generally that the compounds of the present invention are clearly superior plant growth regulators to those of EP No. 0052424 it should be noted that Compound 5 of Table I showed a lower range of activity than the rest of the preferred class in Table X and Compound 12 of Table I in EP No. 0052424 showed a higher range of activity than the rest of the compounds in Table XI. In order to investigate the activity in more detail further side-by-side comparison tests are given in the following Examples and compare representative examples of the present invention with representative examples of EP No. 0052424 and including the above mentioned compounds.

TABLE X

Total Retardation caused by preferred class of compounds of Table I expressed as a percentage of the total retardation caused by paclobutrazol.

| Compound No. | % of paclobutrazol | Cpd. No. | % of paclobutrazol | Cpd. No. | % of paclobutrazol |
|---|---|---|---|---|---|
| 1 | 84.0 | 7 | 58.6 | 13 | 83.3 |
| 3 | 65.6 | 8 | 60.0 |  |  |
| 5 | 28.1 | 9 | 73.9 | 16 | 100.0 |
| 6 | 52.0 | 10 | 47.8 | 17 | 150.0 |

TABLE XI

Total Retardation caused by compounds of Table I of EP 0052424 expressed as a percentage of the Total Retardation caused by paclobutrazol. (* = mean of 2 tests)

| Cpd. No. | % of paclobutrazol | Cpd. No. | % of paclobutrazol | Cpd. No. | % of paclobutrazol | Cpd. No. | % of paclobutrazol |
|---|---|---|---|---|---|---|---|
| 1 | 21.9 | 21 | 7.1 | 36 | 3.6 | 51 | 32.1 |
| 2 | 43.1 | 22 | 47.5 | 37 | 7.1 | 52 | 50.0 |
| 8 | 18.8 | 23 | 36.1* | 38 | 0 | 53 | 30.3 |
| 9 | 18.8 | 24 | 7.1 | 40 | 13.9 | 55 | 21.9 |
| 11 | 21.9 | 25 | 7.1 | 41 | 50.0 |  |  |
| 12 | 62.5 | 26 | 20.1* | 42 | 25.0 |  |  |
| 14 | 31.3 |  |  | 43 | 7.1 |  |  |
| 15 | 37.5 |  |  | 44 | 33.3 |  |  |
| 16 | 44.4 | 29 | 29.0* | 45 | 25.0 |  |  |
| 17 | 28.1 |  |  | 48 | 0 |  |  |
| 19 | 18.8 | 32 | 25.0 | 49 | 3.6 |  |  |
| 20 | 7.1 | 33 | 7.1 | 50 | 3.6 |  |  |

The following Examples 20 and 21 compare representative compounds from the present invention with representative compounds of EP No. 0052424 on side-by-side tests.

EXAMPLE 20

Whole Plant Screen (2)

Compound numbers 1, 5 and 7 (of the present invention) were tested against compounds A, B, C and D (compound Nos. 12, 2, 24 and 50 of Table 1 EP No. 0052424) on whole plant screen (2). The compounds were tested of plant growth regulator activity against five species and for various growth effects relevant to plant growth regulation. The structures are set out in FIG. 1.

Methodology

The plant species used in this screen are presented in Table XII with the leaf stage at which they were sprayed Each chemical was applied at 4000 ppm (4 kg/ha in a 1000 l/ha field volume) using a tracksprayer and a SS8004E (Teejet) nozzle.

After spray the plants were grown in a glasshouse with 25° C. day/22° C. night temperatures and supplementary lighting was supplied when necessary (from mercury vapour lamps), to provide a 16 hour photoperiod. The exception to this were the temperate cereals, wheat and barley which were grown in 16° C. day/13° C. night temperatures.

After 2-6 weeks in the glasshouse, depending on the time of year, the plants were visually assessed for morphological characteristics. Formulation blanks were used as controls to assess the plants. The results are presented in Table XIII.

FIG. 1

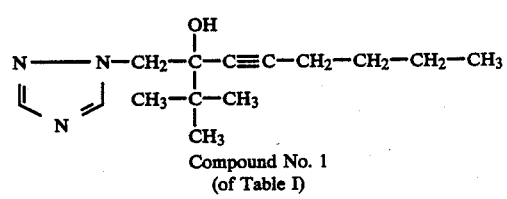

Compound No. 1
(of Table I)

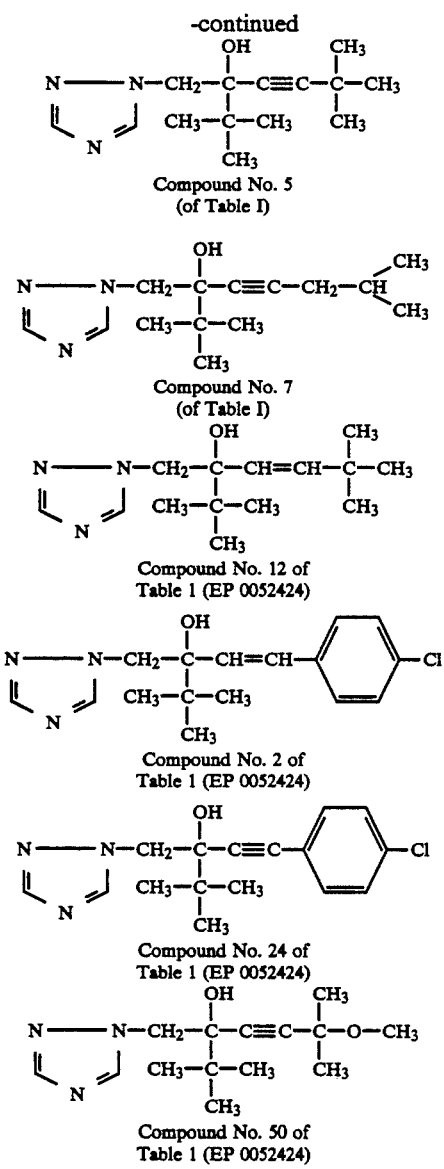

-continued

Compound No. 5
(of Table I)

Compound No. 7
(of Table I)

Compound No. 12 of
Table 1 (EP 0052424)

Compound No. 2 of
Table 1 (EP 0052424)

Compound No. 24 of
Table 1 (EP 0052424)

Compound No. 50 of
Table 1 (EP 0052424)

TABLE XII

PLANT MATERIAL USED FOR WHOLE PLANT SCREEN (2)

| Species | Code | Variety | Growth Stage at Treatment | No. Plants per 3" Pot | Compost Type |
|---|---|---|---|---|---|
| Barley | BR | Atem | 1–1.5 leaves | 4 | JIP* |
| Wheat | WW | Timmo | 1–1.5 leaves | 4 | JIP |
| Maize | MZ | Earliking | 2½ leaves | 1 | PEAT |
| Apple | AP | Red Delicious | 4–5 leaves | 1 | JIP |
| Rice | RC | Ishikari | 2–2½ leaves | 4 | JIP |

JIP* = John Innes Potting Compost.

TABLE XIII

| SPECIES | COMPOUND NO. | R | G | A | T | I |
|---|---|---|---|---|---|---|
| WW | 1 | 2 | | | 1 | 3 |
| | 5 | 2 | 2 | | 2 | 3 |
| | 7 | 2 | 1 | | 1 | 3 |
| | A | 2 | 1 | | | 2 |
| | B | 2 | | | | 3 |
| BR | 1 | 2 | | 1 | | 1 |
| | 5 | | | | | |
| | 7 | 2 | 1 | | | 3 |

TABLE XIII-continued

| SPECIES | COMPOUND NO. | R | G | A | T | I |
|---|---|---|---|---|---|---|
| | A | 1 | | | | |
| | B | 1 | | | 1 | |
| MZ | 1 | | | | | |
| | 5 | | | | | |
| | 7 | | | | | |
| | A | 1 | | | | 1 |
| | B | 1 | | | | 1 |
| RC | 1 | 2 | 2 | | 3 | 3 |
| | 5 | | | | 2 | |
| | 7 | 2 | 1 | | 3 | 3 |
| | A | | | 2 | | |
| | B | 1 | | | | 1 |
| AP | 1 | 3 | 1 | | | 3 |
| | 5 | 3 | | | | 3 |
| | 7 | 1 | 1 | | | 1 |
| | A | 1 | | | | 1 |
| | B | 1 | | | | 1 |

Key:
R = Retardation
G = Greening effect
A = Apical damage
T = Tillering or side shooting
I = Interligular or internodal length reduction
All effects are scored visually on a 1–3 basis where
1 = 10–30%
2 = 31–60%
3 = 61–100%
Blank means less than 10% effect.

EXAMPLE 21

Intermediate Retardant Test

Methodology

Three species are involved in this test RICE, SPRING-BARLEY and APPLES. The variety and growth stages at spray are outlined in Table XIV. Compounds were applied at 1000 ppm and 4000 ppm respectively (1 kg and 4 kg ha$^{-1}$ at a field volume of 1000 l/ha$^{-1}$) as an overall spray. This gives a foliar and root component in the test, i.e. this test will detect the activity of both root and foliar acting compounds. The rice was grown in 4" 'paddy' pots, i.e. the roots and bottom of the stems are immersed in water under conditions corresponding to those in paddy fields. Spring barley and apples were grown in 4" pots. The plants were assessed for height to top-most ligule at approximately 28 days after treatment for spring barley and rice and for height to apex at approximately 28 days after the treatment for apples. The results are presented in Tables XV to XVII. In each case the result for the 1000 ppm and 4000 ppm test for each compound is compared to the height of the formulation blank in that test, and presented as a percentage reduction in height compared to the formulation blank.

TABLE XIV

PLANT MATERIAL FOR INTERMEDIATE RETARDANT TEST

| Species | Variety | Growth Stage at Treatment | No. Plants per 4" Pot | Compost Type |
|---|---|---|---|---|
| Spring Barley | Atem | 3 leaves | 4 | JIP 1 |
| Rice | Ishikari | 3–4 leaves | 2 | SM2:JIP 1 |
| Apples | Red Delicious | 5–10 cm high | 1 | SM2:JIP 1 |

JIP 1 = John Innes Potting Compost.
SM2 = a mixture of loam and grit.

TABLE XV

Percentage Reduction in Height of Spring Barley.
(Compared to formulation blank).

| COMPOUND NO. | Rate 1000 ppm | 4000 ppm |
|---|---|---|
| 1 | 28 | 62 |
| 5 | 9 | 11 |
| 7 | 20 | 51 |
| A | 5 | 13 |
| B | 8 | 7 |
| C | 4 | 6 |
| D | 9 | 13 |

TABLE XVI

Percentage Reduction in Height of Rice.
(Compared to formulation blank).

| COMPOUND NO. | Rate 1000 ppm | 4000 ppm |
|---|---|---|
| 1 | 31 | 53 |
| 5 | 10 | 10 |
| 7 | 27 | 53 |
| A | 4 | 20 |
| B | 3 | 11 |
| C | 5 | 13 |
| D | 2 | 7 |

TABLE XVII

Percentage Reduction in Height of Apples.
(Compared to formulation blank).

| COMPOUND NO. | Rate 1000 ppm | 4000 ppm |
|---|---|---|
| 1 | 0 | 41 |
| 5 | 2 | 24 |
| 7 | 30 | 60 |
| A | 2 | 14 |
| B | 0 | 3 |
| C | 0 | 0 |
| D | 0 | 0 |

The manner in which the compounds of the present invention may be formulated into compositions suitable for application is shown generally in the following indicative illustrations numbered as Examples 22 to 31.

EXAMPLE 22

An emulsifiable concentrate is made up by mixing the following ingredients, and stirring the mixture until all the constituents were dissolved.
  Compound of Table I: 10%
  Calcium dodecylbenzensulphate: 5%
  "SYNPERONIC" NP13: 5%
  "Aromasol" H: 80%

EXAMPLE 23

A composition in the form of grains readily dispersible in a liquid, e.g. water, is prepared by grinding together the first three ingredients in the presence of added water and then mixing in the sodium acetate. The resultant mixture is dried and passed through a British Standard mesh sieve, size 44–100, to obtain the desired size of grains.
  Compound of Table I: 50%
  "Dispersol" T: 25%
  "SYNPERONIC" NP5: 1.5%
  Sodium acetate: 23.5%

EXAMPLE 24

The following ingredients are ground together to produce a powder formulation readily dispersible in liquids.
  Compound of Table I: 45%
  "Dispersol" T: 5%
  "SYNPERONIC" NX: 0.5%
  "Cellofas" B600: 2%
  China clay GTY powder: 47.5%

EXAMPLE 25

The active ingredient is dissolved in acetone and the resultant liquid is sprayed on to the granules of attapulgite clay. The solvent is then allowed to evaporate to produce a granular composition.
  Compound of Table I: 5%
  Attapulgite granules: 95%

EXAMPLE 26

A composition suitable for use as a seed dressing is prepared by mixing the three ingredients.
  Compound of Table I: 50%
  Mineral oil: 2%
  China clay: 48%

EXAMPLE 27

A dusting powder is prepared by mixing the active ingredient with talc.
  Compound of Table I: 5%
  Talc: 95%

EXAMPLE 28

A flowable formulation is prepared by bead-milling the constituents set out below and then forming an aqueous suspension of the ground mixture with water.
  Compound of Table I: 40%
  "Dispersol" T: 4%
  "SYNPERONIC" NP5: 1%
  Water: 55%

EXAMPLE 29

A dispersible powder formulation is made by mixing together the ingredients set out below and then grinding the mixture until all were thoroughly mixed.
  Compound of Table I: 25%
  "Aerosol" OT/B: 2%
  "Dispersol" A.C.: 5%
  China clay: 28%
  Silica: 40%

EXAMPLE 30

This Example illustrates the preparation of a dispersible powder formulation. The ingredients are mixed and the mixture then ground in a comminution mill.
  Compound of Table I: 25%
  "PERMINAL" BX: 1%
  "Dispersol" T: 5%
  Polyvinylpyrrolidone: 10%
  Silica: 25%
  China clay: 34%

EXAMPLE 31

The ingredients set out below are formulated into dispersible powder by mixing then grinding the ingredients.
  Compound of Table I: 25%
  "Aerosol" OT/B: 2%

"Dispersol" A: 5%
China clay: 68%

In Examples 22 to 31 the proportions of the ingredients given are by weight.

There now follows an explanation of the compositions or substances represented by the various Trade Marks and Trade Names mentioned above.

"SYNPERONIC" NP13: a condensate of nonyl phenol (1 mole) with ethylene oxide (13 moles).

"AROMASOL" H: a solvent mixture of alkyl-benzenes.

"DISPERSOL" T AND AC: a mixture of sodium sulphate and a condensate of formaldehyde with sodium naphthalene sulphonoate.

"SYNPERONIC" NP5 a condensate of nonyl phenol (1 mole) with naphthalene oxide (5.5 moles).

CELLOFAS B600: a sodium carboxymethyl cellulose thickener.

We claim:

1. A triazole derivative having the formula (I):

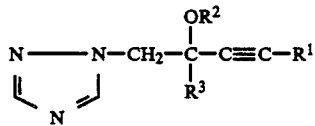

and stereoisomers thereof, wherein $R^1$ is an alkyl group containing from 3 to 6 carbon atoms, or a haloalkyl group containing from 2 to 5 carbon atoms, or a group —$CH_2$—Z wherein Z is a cycloalkyl group containing from 3 to 5 carbon atoms, $R^1$ containing primary or secondary carbon atoms only; $R^2$ is hydrogen or an alkyl group containing from 1 to 4 carbon atoms; and $R^3$ is a tertiary butyl group optionally substituted by halogen; and salts acid addition acetate or benzoate, esters and metal complexes of the compound of formula (I) wherein $R^2$ is hydrogen.

2. A triazole derivative according to claim 1 wherein $R^1$ is an alkyl group containing 4 to 5 carbon atoms or a mono-haloalkyl group containing 3 or 4 carbon atoms or a group —$CH_2$—Z wherein Z is a cyclopropyl or cyclobutyl group.

3. A triazole derivative according to claim 1 wherein the group $R^2$ is hydrogen or a methyl group.

4. A triazole derivative according to claim 1 wherein the group $R^3$ is a tertiary butyl group optionally substituted by a single fluorine, chlorine or bromine atom.

5. A triazole derivative according to claim 1 wherein $R^1$ is an alkyl group containing from 3 to 6 carbon atoms; $R^2$ is hydrogen or an alkyl group containing from 1 to 4 carbon atoms; and $R^3$ is tertiary butyl.

6. A plant growth regulating composition comprising a plant growth regulating amount of a triazole derivative according to claim 1 and an inert carrier or diluent.

7. A method of regulating plant growth which comprises applying to the plant, or to the locus of the plant, a plant growth regulating amount of a triazole derivative according to claim 1.

8. A method according to claim 7 wherein the plants are rice or barley.

* * * * *